United States Patent
Junker et al.

(10) Patent No.: US 11,728,027 B2
(45) Date of Patent: Aug. 15, 2023

(54) SYSTEM OF MEDICAL DEVICES

(71) Applicant: Radiometer Medical ApS, Brønshøj (DK)

(72) Inventors: Thomas Junker, Brønshøj (DK); Jakob Skov, Brønshøj (DE); Halina Tomaszewska, Brønshøj (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 332 days.

(21) Appl. No.: 16/771,785

(22) PCT Filed: Dec. 10, 2018

(86) PCT No.: PCT/EP2018/084205
§ 371 (c)(1),
(2) Date: Jun. 11, 2020

(87) PCT Pub. No.: WO2019/115465
PCT Pub. Date: Jun. 20, 2019

(65) Prior Publication Data
US 2021/0193305 A1    Jun. 24, 2021

(30) Foreign Application Priority Data
Dec. 15, 2017   (DK) .......................... PA 2017 00713

(51) Int. Cl.
*G16H 40/20* (2018.01)
*G16H 10/40* (2018.01)
*G16H 40/40* (2018.01)

(52) U.S. Cl.
CPC .............. *G16H 40/20* (2018.01); *G16H 10/40* (2018.01); *G16H 40/40* (2018.01)

(58) Field of Classification Search
None
See application file for complete search history.

(56) References Cited

U.S. PATENT DOCUMENTS

2008/0270176 A1* 10/2008 Andersen ................ G16Z 99/00
                                                              705/2
2009/0182575 A1    7/2009 Warner et al.
(Continued)

FOREIGN PATENT DOCUMENTS

| EP | 3 091 460 A1 | 11/2016 |
| EP | 3 173 960 A1 | 5/2017 |
| WO | WO 2015/157570 A1 | 10/2015 |

OTHER PUBLICATIONS

International Search Report for International Application No. PCT/EP2018/084205, dated Apr. 12, 2019 (three pages).
(Continued)

*Primary Examiner* — Mohamed A. Wasel
*Assistant Examiner* — Gregory P Tolchinsky
(74) *Attorney, Agent, or Firm* — Finnegan, Henderson, Farabow, Garrett & Dunner, LLP

(57) ABSTRACT

A system of medical devices, the system comprising: a medical device data management system; a plurality of medical devices communicatively connected to the medical device data management system; each medical device being operable to analyze one or more samples of biological material; and to communicate information about an operational state of the medical device to the medical device data management system; a plurality of portable electronic devices, each operable to be carried by an operator, each portable electronic device communicatively connectable to the medical device data management system and configured to receive, from the medical device data management system, information indicative of an operational state of respective medical devices and to display the received information in respect of one or more selected ones of the medical devices.

17 Claims, 5 Drawing Sheets

(56) References Cited

U.S. PATENT DOCUMENTS

| | | |
|---|---|---|
| 2010/0261179 A1 | 10/2010 | Betley et al. |
| 2014/0266713 A1* | 9/2014 | Sehgal .................. G08B 23/00 |
| | | 340/540 |
| 2015/0370975 A1* | 12/2015 | Zebarjadi ............... G16H 40/20 |
| | | 705/2 |
| 2020/0118675 A1* | 4/2020 | Schriver ................ G16H 40/40 |
| 2020/0135333 A1* | 4/2020 | Becker .................. G16H 40/40 |
| 2020/0168339 A1* | 5/2020 | Correnti ................ G16H 50/30 |
| 2020/0185085 A1* | 6/2020 | Mavrieudus ........... G16H 30/40 |
| 2020/0211701 A1* | 7/2020 | Martindale ............ G16H 10/60 |
| 2021/0118555 A1* | 4/2021 | Dreyer ............. G06Q 10/06312 |

OTHER PUBLICATIONS

Written Opinion of the International Searching Authority for International Application No. PCT/EP2018/084205 (seven pages).

* cited by examiner

SYSTEM OF MEDICAL DEVICES

This application is a national stage filing under 35 U.S.C. § 371 of International Application No. PCT/EP2018/084205, filed on Dec. 10, 2018, which claims priority of Danish Patent Application No. PA 2017 00713, filed on Dec. 15, 2017. The contents of these applications are each incorporated herein by reference in their entirety.

TECHNICAL FIELD

The present disclosure relates to a system comprising a plurality of medical devices and a medical device data management system.

BACKGROUND

Modern health care facilities such as hospitals may utilize a variety of medical devices that are operable to analyze samples of biological material, such as body fluids e.g. so as to measure one or more physiological parameters of a patient. Such medical devices are also referred to as analyzers.

In traditional hospital settings, the analysis of samples of biological material was mainly performed by centralized medical laboratories. This often entailed sending off samples away from the point of care and then waiting hours or days to learn the results, during which time care had to continue without the desired information. In modern hospital settings, Point-Of-Care (POC) analysis and testing has become increasingly used. POC analysis and testing generally refers to medical analysis or testing, usually for diagnostic purposes, at or near the point of care—that is, at the time and at or near the place of patient care. The medical devices employed in such a setting are often referred to as POC devices and, in particular, POC analyzers. They are typically located at or near the point of patient care and configured for use by nurses or other healthcare professionals involved with patient care rather than by lab technicians. Moreover, the POC testing and analysis paradigm involves POC analyzers being located throughout the health care facility so as to allow nurses or other healthcare professionals to have quick and easy access to a suitable POC analyzer and to obtain a test/analysis results quickly and conveniently.

It is not uncommon that health care facilities operate a large number of POC analyzers, in some cases up to a hundred POC analyzers or more. These analyzers are often located at different locations throughout the health care facility, i.e. they may be spread out over a relative large area.

Such POC analyzers are frequently operated by nurses or other health care professionals involved in patient care, in the following generally referred to as operators. Typically, an operator obtains a sample of biological material, e.g. a blood sample, from a patient. To this end, the operator may deposit the sample into a suitable container such as a tube, vacuum tube, syringe, capillary tubes, dish or the like, carry the sample to the nearest analyzer that is able to measure the parameters of interest in respect of the sample in question, position the sample in the analyzer, cause the analyzer to perform the desired measurement and record the result.

In many situations, it may be desirable, or even necessary, that the sample, once obtained from the patient, is analyzed within a relatively short time window. This may be because the measurement results may be needed urgently as the results may be critical for deciding on the proper treatment of the patient. Another reason for performing an analysis of a biological sample may be the integrity of the sample. In particular, the biological sample may be unstable and deteriorate once obtained from the patient; this may render an analysis of the sample unreliable, if not useless or even impossible to perform, once too much time has passed between the sample has been obtained and the measurement is performed. In fact, some samples should be analyzed within minutes, e.g. no more than 20 min. or even no more than 10 min. of obtaining the sample from the patient.

Examples of particularly sensitive samples are blood samples to be analyzed for blood gases, such as $O_2$ and $CO_2$, by a blood gas analyzer. Therefore blood samples to be analyzed for such blood gases are normally collected in a closed container, in order that the subsequent blood gas analysis is not unduly affected due to contact of the blood sample with ambient air. Nevertheless, blood gas analyses are often sensitive to delays between the collection of the sample, and the analysis.

Modern POC analyzers often require regular maintenance, such as calibration, cleaning or the like. Typically, an analyzer is not able to perform measurements while maintenance is ongoing. Moreover, an analyzer may be out of service, e.g. waiting for maintenance personnel. Accordingly, when an operator arrives at an analyzer, the operator may realize that the analyzer is currently undergoing maintenance, is out of service or occupied by another measurement task. Hence, the operator may either have to wait for the maintenance or ongoing measurement task to finish or decide to go to another analyzer which may be relatively far away from the originally selected analyzer. Hence, in both cases the operator wastes valuable time. Moreover, if the operator decides to go to another analyzer, the other analyzer may also be currently unavailable, e.g. due to an ongoing maintenance task or an ongoing measurement.

As a result, the analysis task is inefficient and there is a risk that samples are wasted because they are not analyzed in due time. Hence, in addition to the delay in obtaining a measurement result, a new sample may have to be obtained—a process that requires additional time, resources and may be unpleasant or even dangerous for the patient. These issues may be particularly undesirable when performing measurements on blood samples from patients where blood management is critical, e.g. on very ill patients or neonates.

It would thus be desirable to provide a system of medical devices that solves, or at least reduces at least some of the above problems.

SUMMARY

Disclosed herein are embodiments of a system of medical devices, the system comprising:

a medical device data management system;

a plurality of medical devices communicatively connected to the medical device data management system; each medical device being operable to analyze one or more samples of biological material and to communicate information about an operational state of the medical device to the medical device data management system;

a plurality of portable electronic devices, each operable to be carried by an operator, each portable electronic device communicatively connectable to the medical device data management system and configured to receive, from the medical device data management system, information indicative of an operational state of respective medical devices and to display the received information in respect of one or more selected ones of the medical devices.

Accordingly, the individual operator is provided with updated information about the current availability of selected medical devices. This allows the operator to choose a suitable medical device for analyzing an obtained sample of biological material and the risk is reduced that the chosen medical device is not available for performing the required analysis when the operator arrives with the sample at the medical devices.

In some embodiments, the medical device data management system is configured to transmit updated information about the operational state of at least the selected medical devices to the portable electronic device in real-time, so as to allow the portable electronic device to display real-time updated information about the operational state of the selected medical devices. Here the term real-time updated information is intended to refer to updated information where the delay between the receipt of information by the medical device data management system about a change of an operational state of a selected medical device and the display of the updated information by the portable electronic device is less than 10 minutes, such as less than 5 minutes, preferably less than 1 minute. Preferably the system is configured such that the delay between the occurrence of a change of the operational state of the selected medical device and the display of the updated information is less than 10 minutes, such as less than 5 minutes, preferably less than 1 minute. Accordingly, the operator of the portable electronic device is able to determine the current availability and the expected availability of the operator's preferred medical devices in real-time, e.g. when the operator obtains, or is about to obtain, a sample of biological material from a patient.

The medical devices may be analyzers for analyzing blood samples, such as a blood gas analyzers, or analyzers for analyzing other types of samples of biological material. In particular, the medical devices may be POC devices, e.g. POC blood gas analyzers, configured to be operated by nurses or other health care professionals normally involved in patient care and, in particular, health care professionals normally obtaining the samples from the patients. Generally POC devices are devices that are positioned at or near the point of patient care such as within few minutes walking distance of a patient point of care.

The medical device data management system may be a suitably configured data processing system. In particular, the medical device management system may comprise a suitably programmed data processing system, configured to communicate with multiple medical devices, e.g. medical devices of different device manufacturers, and to provide functionality for monitoring the medical devices, to log, store and/or to otherwise process data from the medical devices.

Many health care facilities utilize a data processing system that is operable to manage data related to various operational aspects of the health care facility such as one or more of the following: medical, administrative, financial, and compliance issues and the corresponding processing of services. Such a data processing system is often referred to as hospital information system (HIS). Depending on the scope of the function of the data processing system, such a system may also be referred to as a laboratory information system (LIS), a radiology information system (RIS) or the like. For the purpose of the present description, such systems will collectively be referred to as health care facility information systems.

Data from various medical devices and, optionally, from other devices are typically fed into a health care facility information system. Examples of such data may include measurement results, usage data, error messages and/or other information from medical device to the health care facility information system. A health care facility information system may include one or more software and/or hardware components. One example of such components may be a medical device data management system as described herein. In other embodiments the medical device data management system may be separate from the health care facility information system, e.g. a system communicatively connected to the health care facility information system.

One example of a medical device data management system includes a computer system executing a software program that is marketed under the name "AQURE" Enterprise POC data management system by Radiometer Medical Aps, Denmark. Generally, a medical device data management system may be configured to communicate with a plurality of medical devices and to provide functionality for monitoring an operational status of said medical devices, e.g. to present status indicators associated with the respective medical devices to e.g. lab managers, maintenance personnel etc. Examples of parameters indicative of an operational status that may be presented by a medical device data management system include one or more of the following: error indicators, calibration information, information indicative of required QC procedures, information about required maintenance, and/or the like.

In embodiments of the system disclosed herein, the medical device data management system is further configured to communicate with a plurality of portable electronic devices, separate from the medical device management system, each operable to be carried by an operator and each communicatively connectable to the medical device data management system. In particular, the medical device data management system is configured to communicate information indicative of an operational state of one or more medical devices to respective portable electronic devices so as to allow or even cause the portable electronic devices to display the received information in respect of respective selected one or more medical device, thus providing personalized and up to date availability information about the available medical devices to the operators when the operators obtain samples to be analyzed.

The selection of medical devices about which information is to be displayed on a portable electronic device may be made by the medical device data management system and/or by the respective portable electronic devices.

In particular, in some embodiments, the medical device management system may be configured to select one or more medical devices information associated with a portable electronic device and to communicate information of an operational state of only the selected medical devices to said portable electronic device. Accordingly, the amount of data that has to be communicated from the medical device data management system to the respective portable electronic devices is reduced.

In some embodiments, the portable electronic device may select a subset of medical devices about whose operational state information has been received and display the received information only for the selected subset of medical devices. Hence, the user may change the selection of which medical devices are to be displayed without the need for transmitting additional information in respect of previously non-selected medical device.

Alternatively or additionally, the medical device data management system and/or the portable electronic device may determine a prioritized order in which the information received by the portable electronic device is displayed.

In any event, the selection of medical devices about which information is to be displayed on a portable electronic device may be based on one or more selection criteria, e.g. responsive to one or more criteria chosen from the following criteria: identify an operator associated with the portable electronic device, a current location and/or another attribute associated with said operator, a current location and/or another attribute of the portable electronic device, locations and/or other attributes of the medical devices, a current time, or a combination thereof. The selected medical devices may be a true subset of all medical devices communicatively connected to the medical device data management system. The selection of medical devices displayed on respective portable electronic devices may be specific to the respective portable electronic device. The selection criteria may be the same for all portable electronic devices, e.g. for each portable electronic devices the selection may be based on the identity of the operator associated with said portable electronic device. In other embodiments the selection criteria may vary between portable electronic devices or between operators. For example, some operators may prefer that medical devices are selected based on their location while other operators may have a fixed list of favorite medical devices to be displayed. The selection criteria may be based on one or more of the following:

information stored by the medical device data management system, e.g. locations of respective medical devices, operator profiles, information about scheduled maintenance tasks, usage histories of medical devices and/or operators, etc.

information received from the medical devices, e.g. usage logs, information about, location information, etc.

information received from the portable electronic devices, e.g. information about a current operator associated with the portable electronic device, location information about the portable electronic device, etc.

information from other sources, e.g. from a computer network, e.g. information about access points to which portable electronic devices and/or medical devices are connected to.

In particular, in some embodiments, the selected medical devices about which information is displayed in a portable electronic device may be selected based on an identity of an operator associated with said portable electronic device. The operator associated with the portable electronic device may e.g. be an operator who has completed a login process on the portable electronic device or has otherwise identified himself/herself to the portable electronic device where the operator provides a user name or other suitable information for identifying the operator. As mentioned above, the selection may be made by the portable electronic device or by the medical device data management system. To this end, each portable electronic device may communicate information about an operator associated with said portable electronic device to the medical device data management system. The portable electronic device may communicate the identity of the operator associated with the device to the medical device data management system as part of the login process and or as part of a request to receive information from the medical device data management system. The selected medical devices may e.g. be selected based on an operator profile stored by the medical device data management system or by the portable electronic device, where the operator profile identifies the selected medical devices. In some embodiments, the medical device data management system may select the medical devices for an operator based on a usage history of the operator, e.g. by selecting, for a given operator, the most frequently used medical devices and/or the most recently used medical devices. To this end, the medical device data management system may receive usage data from the respective medical devices, the usage data including information about which operators have used the medical device to perform an analysis. In particular, the medical devices may be configured to receive, when initiating an analysis of a biological sample, information identifying an operator who requests the analysis. Based on the received usage data, the medical device data management system may select a subset of medical devices to be associated with an operator and communicate information about the selected medical devices to the portable electronic device associated with the operator. As some health care facilities may include a large number of medical devices, in some cases hundreds of medical devices, displaying only information about a selected subset of medical devices on a portable electronic device allows the operator to identify a suitable medical device more quickly, in particular if the selected subset is operator-specific and selected based on an operator profile and/or usage history of the operator.

Accordingly, in some embodiments, the medical device data management system is configured to:

obtain (e.g. from usage data received from the medical devices) usage data associated with an operator, the usage data being indicative, for at least a subset of medical devices, of a frequency of use of each of said subset of medical devices by said operator;

select one or more of the medical devices to be associated with said operator based at least in part on the obtained usage data; and transmit, to a portable electronic device associated with said operator, information indicative of an operational state of the selected one or more medical devices for display by said portable electronic device.

In some embodiments, the medical device data management system or the portable electronic device may select the medical devices about which information is to be displayed by the portable electronic device at least in part based on information about the portable electronic device, such as information about display capabilities of the portable electronic device, a current location of the portable electronic device, and/or the like. To this end, the medical device data management system may obtain information about a current location of the portable electronic device. For example, the portable electronic device may be wirelessly connected to the medical device data management system via a wireless access point, and the medical device data management system may obtain information identifying said wireless access point or otherwise use Wi-Fi position monitoring or the like. In other embodiments, the portable electronic device may be configured to obtain information about its own location, e.g. by means of a Wi-Fi positioning system, and communicate said information to the medical device data management system. In any event, the medical device data management system may select medical devices in a proximity of the current location of the portable electronic device.

In some embodiments, the medical device data management system or the portable electronic device may select the medical devices about which information is to be displayed by a portable electronic device at least in part based on information about the sample to be analyzed, such as a type of analysis to be performed, an identifier identifying the patient from which the sample was taken and/or the like. The information about the type of analysis to be performed may e.g. be entered into the portable electronic device by the operator and, optionally forwarded to the medical device data management system. Similarly, the patient information may be entered by the operator into the portable electronic device, e.g. manually via a suitable user interface, by scanning a barcode or other identifying tag, such as an RFID tag, a QR code, etc. that is associated with the patient, e.g. in the form of a wristband, attached to a hospital bed, etc. In any event, the portable electronic device may communicate information about the sample to be analyzed to the medical device data management system, and the medical device data management system may select a subset of medical devices at least in part based on said information. For example, the medical device data management system may select only medical devices that have the capability to perform a desired type of analysis. The medical device data management system may also obtain information about a location of the patient and select medical devices in a proximity of the location. Alternatively, the portable electronic device may perform the selection based at least in part on information received from the medical device data management system.

In some embodiments, the information about an operational state received by the portable electronic device from the medical device data management system includes an availability prediction indicative of a predicted availability of the medical device for performing an analysis. The availability prediction may be indicative of an estimated duration until the medical device is available for operation and/or an estimated duration until the medical device is unavailable for operation. Accordingly, the portable electronic device may display the availability prediction and/or sort a displayed list of selected medical devices based at least in part on the received availability prediction. This allows a user to more easily select a medical device that is likely capable of performing a desired analysis at this point in time, e.g. before the quality of the sample to be analyzed diminishes. The availability prediction may e.g. be in the form of an estimated duration until the medical device is available again, if the medical device is currently unavailable, or a predicted time, when the medical device is available again. Alternatively or additionally, the availability prediction may e.g. be in the form of an estimated duration a sample is expected to wait in a queue until being analyzed. Yet alternatively or additionally, the availability prediction may e.g. be in the form of an estimated duration until the medical device is expected to become unavailable, if the medical device is currently available, or a predicted time, when the medical device is expected to become unavailable.

In some embodiments, the portable electronic device or the medical device data management system may be configured to obtain a time stamp indicative of when the sample was obtained. For example, the time stamp may be determined from an operator input to the portable electronic device, e.g. the operator initiating a sample acquisition function on the portable electronic device, the operator entering (e.g. scanning a barcode or the like) information identifying a sample and/or a patient, or the operator entering other information pertaining to the acquisition of a sample from a patient. Based on the obtained time stamp, the portable electronic device or the data management system may further determine and, optionally, display on the portable electronic device information about a time at which the sample should be analyzed at the latest in order to ensure the integrity of the sample. The time may e.g. be determined based on predetermined standards for the health care facility and/or based on other conditions. Moreover, the portable electronic device or the data management system may use the determined time information to indicate to the operator which of the selected medical devices are expected to be able to perform an analysis of the sample within the determined time.

In some embodiments, the medical device data management system is configured to determine the availability prediction based at least in part on information received from the medical devices.

To this end, in some embodiments, each medical device is configured to communicate an availability prediction to the medical device data management system. The availability prediction sent by a medical device may e.g. include information about scheduled maintenance events and/or said estimated duration. Accordingly, the medical device data management system may forward accurate availability predictions for the individual medical devices to the portable electronic device.

In some embodiments, the medical device data management system is configured to:
obtain usage data associated with at least a subset of medical devices, the usage data being indicative of a frequency of use of each of said subset of medical devices; and
determine the availability prediction at least in part based on the obtained usage data.

Accordingly, a more accurate availability prediction may be computed. The usage data may be received from the respective medical devices or at least be determined from information received from the respective medical devices, e.g. from usage logs indicative of performed analysis tasks including the times at which the tasks have been performed. The medical device data management system may thus determine a typical workload of the various medical devices at respective times, e.g. at respective times of day. The medical device data management system may thus compute an estimated time a sample will have to wait in a queue before being analyzed.

In some embodiments, the medical device data management system may even compute an estimated time a sample will have to wait in a queue before being analyzed based on current, e.g. real-time, information from the medical devices, e.g. information about a current workload.

Accordingly, in some embodiments, a first one of the medical devices comprises multiple sample bays, each sample bay configured to receive a sample (either directly or accommodated in a sample container or holder) of biological material to be analyzed by the first medical device; wherein the first medical device is configured to analyze samples positioned in the sample bays in a sequential order so as to implement a queue of said samples placed in the sample bays and awaiting analysis by the first medical device; wherein the first medical device is configured to communicate information indicative of a current status of said queue to the medical device data management system; and wherein the medical device data management system is configured to determine the operational state of the first medical device from at least the communicated information indicative of said current status of said queue.

The availability prediction may be a global prediction for the entire medical device and/or a it may be a specific prediction for one or more specific analysis tasks a medical device is capable of performing, e.g. an availability prediction for the measurement of a certain physiological parameter.

In some embodiments, one or more of the portable electronic devices are configured to transmit, to the medical device data management system, an indication of an intended measurement to be taken on a biological sample by an operator associated with the portable electronic device; and wherein the medical device data management system is configured to determine the availability prediction at least in part based on the information received from the medical devices and on the indications received from the one or more portable electronic devices.

For example, the indication of an intended measurement may include an indication of a type of measurement to be performed, and the medical device data management system may compute an availability prediction that is specific for said type of measurement.

Alternatively or additionally, the medical device data management system may utilize information about received indications of intended measurements in order to otherwise improve the availability prediction. For example, based on the received indications, the medical device data management system may compute an expected future workload of the medical devices for the immediate future, e.g. for the next 20 minutes or for another suitable time window. More particularly, the medical device data management system may compute the expected future workload from historic usage data (indicating a typical workload e.g. for a given time of day) and the received indications, e.g. by adjusting the typical availability prediction upwards or downwards. In some embodiments, the indication of an intended measurement may include an indication of an intended medical device at which the operator intends to perform an analysis. For example, such an indication may be based on a suitable operator input. In one embodiment, the user interface of the portable electronic device may be configured to record a user selection of a medical device, e.g. from a displayed list of medical devices. For example, the user may tap on an entry of a displayed list of medical devices in order to select a medical device and communicate that the operator intends to perform a measurement on the selected medical device. Upon receipt of indications of intended measurements from respective portable electronic devices, the medical device management system may thus compute a current estimated workload and, hence, an estimated current availability prediction for the respective medical devices. The indications of intended measurements reflect expected analysis tasks to be performed by the respective medical devices in the near future, e.g. after the time it takes to prepare the sample and/or for the operator to transport the sample to the selected medical device. The current availability prediction may thus be indicative of an expected waiting period/work load of a medical device during a period of time in the near future, e.g. within the next 10-20 min or another suitable time period. For example, to this end, the medical device data management system may compare the number of received indications of intended measurements with a typical number (e.g. a typical number for a certain day, a certain time of day, or the like) of analyses performed by a medical device and adjust the availability prediction accordingly.

In some embodiments, e.g. where the indication of an intended measurement does not include any indication of any intended medical device, the medical device data management system may compute an estimated current global workload for all medical devices or weigh the estimated workload for different medical devices based on other parameters. For example, the medical device data management system may correlate an indication of an intended measurement received from an operator's portable electronic device with information about which medical devices are typically used by said operator. This may e.g. be based on a stored operator profile or on usage data received from the medical devices.

In some embodiments, the medical device data management system is configured to:
  obtain device location information about respective locations of at least a subset of medical devices and operator location information about a location of said operator;
  determine the availability prediction at least in part on the information received from the medical devices, on the indications received from the one or more portable electronic devices and on the obtained device location information and operator location information.

Accordingly, the medical device data management system may compute a further improved availability prediction. To this end, the medical device data management system may use the received indications and location information in a number of ways. For example, when the medical device data management system receives a number of indications of intended measurements from operators in a vicinity of a first medical device, the medical device data management system may adjust the estimated duration as to when an operator may expect to be able to have a sample analyzed by said first medical device upwards. Alternatively or additionally, the medical device data management system may determine a most likely medical device where the operator intends to perform the analysis, in particular the medical device closest to the operator. This may be particularly suitable when the indication from the operator does not include an indication of any medical device. Yet alternatively or additionally, the medical device data management system may determine an estimated time when the intended measurement will be performed based on the distance between the operator and the selected or closest medical device, thus allowing for a more accurate prediction of the expected workload of the respective medical devices within the near future.

Generally, information about the respective locations of the medical devices within the health care facility may be used in a number of ways. When the medical devices typically remain at the same location within a health care facility, the device locations may be recorded in a configuration setup of the medical device data management system, or as an attribute of a database record of a database including information about the respective medical devices, or in another suitable manner. If the medical devices are frequently moved around, it may be expedient to detect their locations automatically, e.g. by detecting which wireless access point they connect to, by a Wi-Fi positioning system, or the like.

Specifically, in some embodiments, the medical device data management system is configured to:
  obtain device location information about respective locations of at least a subset of medical devices;
  select one or more of the medical devices based at least in part on the obtained device location information and on an identity of an operator associated with the one of the portable electronic devices; and
  transmit, to said portable electronic device associated with said operator, information indicative of an operational state of the selected one or more medical devices for display by said portable electronic device.

For a given operator, the medical device data management system may select a subset of medical devices for which information is to be displayed on the operator's portable electronic device. In particular, the selection may be based on the location of the respective medical devices, e.g. relative to a normal workplace, e.g. a department, ward, etc.

of the operator. The normal workplace of the operator may e.g. be stored as part of an operator profile that is accessible to the medical device data management system.

In a further embodiment, the medical device data management system is configured to:

obtain dynamic operator location information about a current location of said operator;

select the one or more of the medical devices to be associated with said operator based at least in part on the obtained device location information and the obtained operator location information.

Hence, the selection of which medical devices to be displayed on an operator's portable electronic device may be based on a location of the respective medical devices relative to an actual current location of the operator. This may be more accurate than a static indication of a normal workplace of the operator, as operator's may frequently change their actual position within a health care facility. The dynamic operator location information may be obtained when the operator logs in or otherwise registers himself/ herself at a given location within the health care facility. Alternatively or additionally, the dynamic operator location may be determined as a device location of a portable electronic device associated with the operator, e.g. by Wi-Fi location monitoring or by detecting a location of a wireless access point via which the portable electronic device accesses a wireless computer network. Hence, generally, the medical device data management system may be configured to obtain a location of a portable electronic device associated with the operator and to determine the dynamic operator location information to coincide with the obtained location of the portable electronic device.

The present disclosure relates to different aspects including the system described above and in the following and to corresponding methods, apparatus and products, as described above and in the following. Each aspect may yield one or more of the benefits and advantages described in connection with one or more of the other aspects, and each aspect may have one or more embodiments with all or just some of the features corresponding to the embodiments described in connection with one or more of the other aspects and/or disclosed in the appended claims.

In particular, the present disclosure further relates to a medical device data management system communicatively connectable to a plurality of medical devices, each medical device being operable to analyze one or more samples of biological material; and to a plurality of portable electronic devices, each configured to receive, from the medical device data management system, information indicative of an operational state of one or more selected ones of the medical devices and to display the received information; wherein the medical device data management system is configured to:

receive information about operational states of respective ones of the medical devices;

communicate information indicative of an operational state of one or more selected ones of the medical devices to a selected one of the portable electronic devices.

Embodiments of a medical device data management system may be implemented as a suitably programmed data processing system, e.g. comprising one or more computers. The data processing system may have stored thereon a suitable computer program which, when executed by the data processing system, causes the data processing system to perform one or more of the functions described herein. The medical device data management system may comprise a server computer and one or more client terminals. For example, the server computer may have stored thereon a suitable computer program which, when executed by the server computer, causes the server computer to perform one or more of the functions described herein. The server computer may be implemented as one or more virtual machines.

The medical device data management system may be connectable to the medical devices via any suitable wired and/or wireless connection, e.g. a wired and/or wireless computer network such as a local area network. To this end, the communications interface of the medical device data management system may comprise any suitable device or circuit for communicatively connecting the medical device data management system to such a computer network, e.g. a suitable network adapter.

Similarly, the medical device data management system may be connectable to the portable electronic devices via any suitable wired and/or wireless connection, e.g. a wired and/or wireless computer network such as a local area network. To this end, the communications interface of the medical device data management system may comprise any suitable device or circuit for communicatively connecting the medical device data management system to such a computer network, e.g. a suitable network adapter. As the portable electronic devices are portable, it is preferred that at least the portable electronic devices are wirelessly connectable to said computer network, e.g. via Wi-Fi, Bluetooth or another suitable wireless technology.

The medical device data management system may be operable to process data received from medical devices and from a facility information system, e.g. for allowing presentation of such data via a suitable user interface. Examples of data that is presented to the user by the medical device data management system may include one or more of the following: information about which medical devices are connected to the medical device data management system and, optionally, their status, information about quality control measurements, patient observation results, etc. It will be appreciated that, in alternative embodiments, the medical device data management system may be operable to perform additional or alternative functions. The medical device data management system may comprise a suitable communications interface for communicating with a facility information system and one or more suitable device communications interface for communicating with respective medical devices. The device communications interfaces may include one or more suitable device drivers.

It is noted that the features of embodiments of the methods performed by the apparatus and devices of the system described herein may be implemented in software and carried out by a data processing system caused by the execution of program code means such as computer-executable instructions. Here and in the following, the term data processing system comprises any circuit and/or apparatus suitably adapted to perform the above functions. In particular, the above term comprises general—or special-purpose programmable microprocessors, Digital Signal Processors (DSP), Application Specific Integrated Circuits (ASIC), Programmable Logic Arrays (PLA), Field Programmable Gate Arrays (FPGA), special purpose electronic circuits, etc., or a combination thereof.

In particular, according to one aspect, a computer program product comprises executable program code configured, when executed by a medical device data management system communicatively connectable to a plurality of medical devices, each medical device being operable to analyze one or more samples of biological material, and to a plurality of portable electronic devices, each configured to receive, from the medical device data management system, information indicative of an operational state of one or more selected ones of the medical devices and to display the received information, to cause the medical device data management system to:

receive information about operational states of respective ones of the medical devices;

communicate information indicative of an operational state of one or more selected ones of the medical devices to a selected one of the portable electronic devices.

For example, the program code may be loaded into a memory, such as a RAM (Random Access Memory), from a storage medium or from another computer via a computer network. Alternatively, some or all of the described features may be implemented by hardwired circuitry instead of software or in combination with software. The computer program may be embodied as a tangible storage medium having stored thereon the computer program or as a data signal encoding the computer program. Examples of a tangible storage medium include a hard disc, an optical disc, a compact disc, a DVD, a memory stick, a memory card, an EPROM, and/or the like.

According to yet another aspect, disclosed herein are embodiments of a portable electronic device comprising a communications interface for data communication between the portable electronic device and a medical device data management system; a processor and a display; wherein the processor is configured to:

receive, from the medical device data management system via the communications interface, information indicative of an operational state of one or more selected ones of a plurality of medical devices connected to the data management system, each medical device being operable to analyze one or more samples of biological material; and to display on said display the received information.

The term portable electronic device is intended to comprise any portable device comprising a processor, such as a microprocessor or other form of CPU, for data processing. In particular, the above term is intended to comprise any portable radio communications equipment, and other portable devices, personal computers or other computers or data processing systems. In particular, a portable electronic device may be a handheld electronic device. Embodiments of the portable electronic device may comprise a respective communications interface adapted for communicating data to the medical device data management system, e.g. via a wired or a wireless communications channel, such as a local area network, e.g. a wireless local area network, a wide area network, an internet, a telecommunications network such as a cellular communications network, a short range wireless communications interface, a serial or parallel interface, a USB interface, a Bluetooth interface, and/or the like.

The term portable radio communications equipment includes handheld radio communications equipment such as mobile terminals, e.g. mobile telephones, pagers, communicators, electronic organizers, smart phones, personal digital assistants (PDAs), handheld computers, or the like.

Embodiments of the portable electronic device may further comprise a display or other suitable user interface. Embodiments of the portable electronic device may further comprise input means for receiving identifiers; for example, the input means may include a reader for reading a machine readable code such as a barcode scanner, a reader for reading radio-frequency identification (RFID) tags or labels, a user-interface allowing manual input of identifiers, a camera, or any other suitable input means.

According to yet another aspect, disclosed herein are embodiments of a computer program product comprising executable program code configured, when executed by a processor of a portable electronic device, the portable electronic device comprising a communications interface for data communication between the portable electronic device and a medical device data management system, the processor and a display, to cause the processor to:

receive, from the medical device data management system via the communications interface, information indicative of an operational state of one or more selected ones of a plurality of medical devices connected to the data management system, each medical device being operable to analyze one or more samples of biological material; and to display on said display the received information.

For example, the program code may be loaded into a memory, such as a RAM (Random Access Memory), from a storage medium of the portable electronic device or from another computer via a computer network. Alternatively, some or all of the described features may be implemented by hardwired circuitry instead of software or in combination with software. In some embodiments, the portable electronic device may comprise a suitable smartphone, a tablet or the like, and the computer program may be implemented as an App that is executable by the portable electronic device.

Generally, a computer program may be embodied as a tangible storage medium having stored thereon the computer program or as a data signal encoding the computer program. Examples of a tangible storage medium include a hard disc, an optical disc, a compact disc, a DVD, a memory stick, a memory card, an EPROM, and/or the like.

Other systems, apparatus, methods, products and features of the present invention will become apparent to one having ordinary skill in the art upon examining the following drawings and detailed description. It is intended that all such additional systems, apparatus, methods, products and features be included in this description, be within the scope of the present invention and be protected by the accompanying claims.

BRIEF DESCRIPTION OF THE DRAWINGS

The above as well as additional objects, features and advantages of the aspects disclosed herein will be better understood through the following illustrative and non-limiting detailed description of preferred embodiments, with reference to the appended drawings, where like reference numerals will be used for like elements.

The accompanying drawings are included to provide a further understanding of the aspects disclosed herein, and they are incorporated in, and constitute a part of, this specification. The drawings illustrate embodiments of the aspects disclosed herein and, together with the description, serve to explain the principals of the aspects disclosed herein. Other and further aspects and features will be evident from reading the following detailed description of the embodiments. These drawings depict only typical embodiments and are not therefore to be considered limiting of its scope.

DETAILED DESCRIPTION

Figure 1:
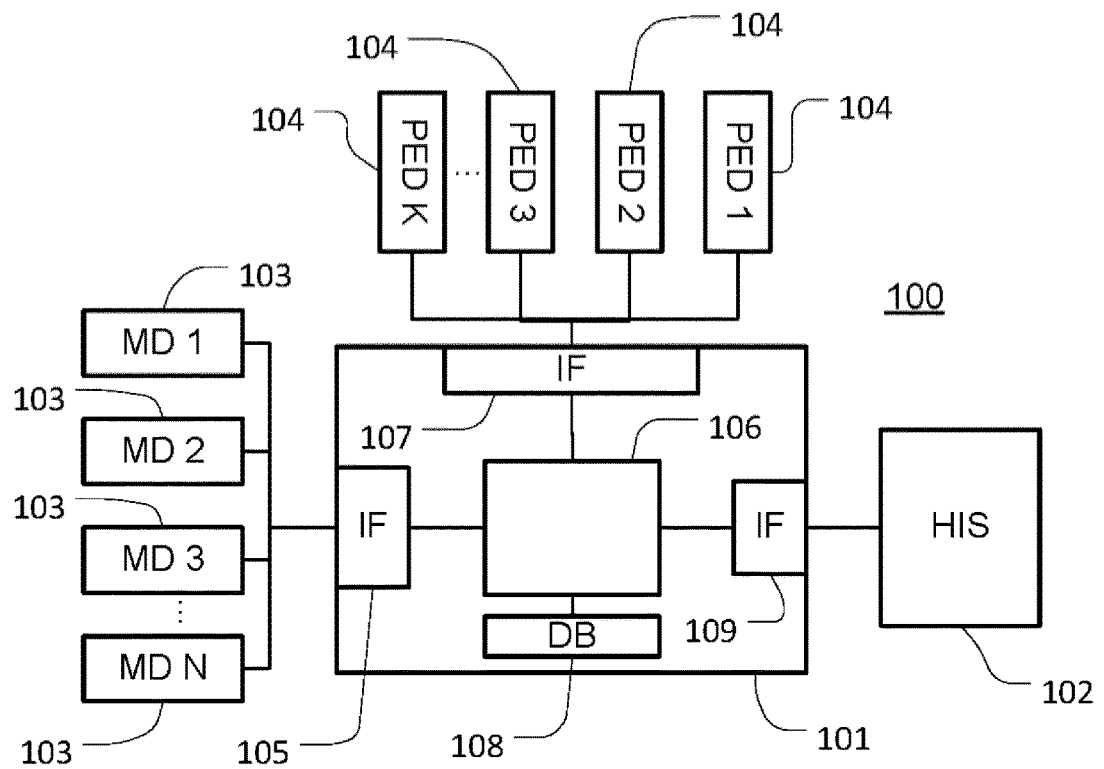
FIG. 1 schematically illustrates an embodiment of a system comprising a plurality of medical devices, a medical device data management system and a plurality of portable electronic devices.

FIG. 1 schematically illustrates an embodiment of a system that comprises a medical device data management system 101, a number of medical devices 103, each in communicative connection with the medical device data management system 101, and a number of portable electronic devices 104, each in communicative connection with the medical device data management system 101. Optionally, the system further comprises a facility information system 102 such as a hospital information system (HIS) in communicative connection with the medical device data management system 101.

The portable electronic devices 104 are connectable to the medical device data management system 101 via suitable communications links, e.g. via a wireless communications network such as a wireless local area network. In the example of FIG. 1, four portable electronic devices are shown but it will be appreciated that, while a system with only four or less portable electronic devices is possible, typical systems include more than four portable electronic devices, such as considerably more portable electronic devices, e.g. several tens or hundreds of portable electronic devices. The portable electronic devices may be identical with each other or different from each other, and they may be connectable to the computer network in a variety of different ways, e.g. by means of a suitable wireless connection.

Figure 2:
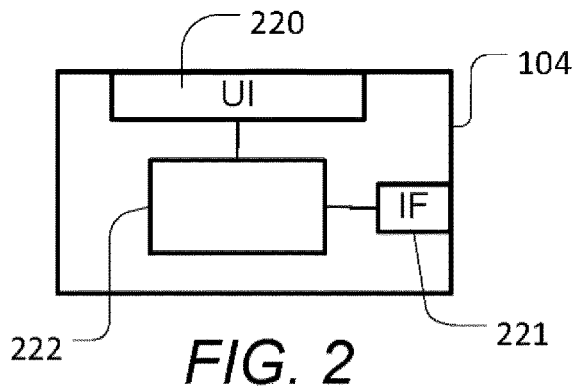
FIG. 2 schematically illustrates an embodiment of a medical device.

FIG. 2 illustrates a schematic block diagram of an embodiment of a portable electronic device 104. The electronic device 104 comprises a processing unit 222, e.g. including a suitably programmed microprocessor or other suitable processing means, communicatively coupled to a communications interface 221. The electronic device 104 further comprises a user interface 220, such as a touch-sensitive display or a display and one or more buttons and/or other forms of user input devices. The user interface 220 is also communicatively coupled to the processing unit 222. The processing unit 222 may further comprise a suitable data storage device for storing computer programs and other data, e.g. a RAM, an EPROM, etc. Examples of a portable electronic device include a tablet computer or a smartphone having stored thereon a suitable computer program such as an App. The communications interface 221 may be a wireless network adapter, a Bluetooth transceiver or any other suitable device or circuit allowing wireless data communication with the medical device data management system, e.g. via a suitable computer network.

Again referring to FIG. 1, the medical devices 103 are analyzers for analyzing samples of biological material. Examples of a medical device a blood glucose meter, a blood gas analyzer, an analyzer for measuring cardiac, coagulation, infection and/or pregnancy markers, and/or the like. It will be appreciated that embodiments of the system may include other types of medical devices, such as patient monitoring systems or the like.

Figure 3:
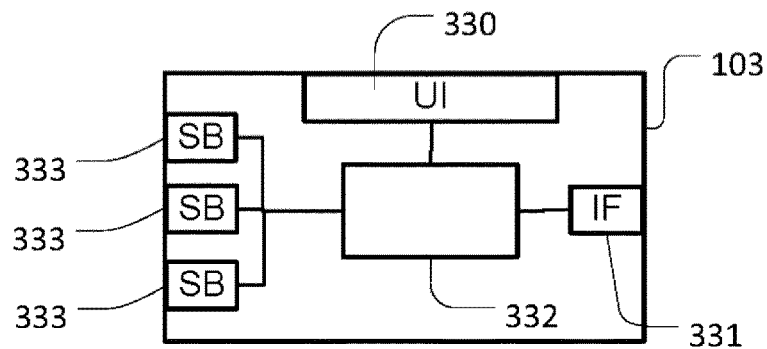
FIG. 3 schematically illustrates an embodiment of a portable electronic device.

FIG. 3 illustrates a schematic block diagram of an embodiment of a medical device 103. The medical device 103 comprises an analysis unit 332 communicatively coupled to a communications interface 331. The communications interface 331 may be a wired or wireless network adapter, a Bluetooth transceiver or any other suitable device or circuit allowing wired and/or wireless data communication with the medical device data management system, e.g. via a suitable computer network.

The medical device 103 further comprises a user interface 330, such as a touch-sensitive display or a display and one or more buttons and/or other forms of user input devices. The user-interface allows a user to interact with the medical device, e.g. so as to select the type of analysis to perform, to enter information pertaining to a sample, to view results of the analysis, etc.

The medical device 103 further comprises a number of sample beds 333 operationally coupled to the analysis unit 332. In the example of FIG. 3, the medical device includes three sample beds; it will be appreciated, however, that alternative embodiments of medical devices may include a single sample bed or a different number of sample beds. Each sample bed 333 is configured to receive a sample of biological material, e.g. a test tube or other suitable container accommodating a sample, such as a body fluid, e.g. a blood sample, a urine sample, etc. Generally, in the context of an analyser for analysing blood samples, a sample may be contained in a sampler, i.e. a syringe, a vacuum tube, a test tube, a capillary tube or similar device for collecting blood.

The analysis unit 332 is configured to access a sample positioned in one of the sample beds, e.g. by withdrawing or otherwise receiving a sample from one of the sample beds via a suitable inlet, and to perform one or more measurements on the accessed sample, e.g. using a suitable analysis method known as such in the art. The analysis unit may further comprise a suitably programmed microprocessor or other suitable processing means configured to control operation of the analysis unit 332, the sample beds 333, the communications interface 331 and the user-interface 330. The analysing unit may further comprise a suitable data storage device for storing data, e.g. a RAM, an EPROM, a hard disk, etc. In particular, the analysis unit may be configured to display one or more results of an analysis on the user interface 330 and to forward information pertaining to respective analysed samples as well as other operational data to the medical device data management system.

Examples of information pertaining to an analysed sample include one or more of the following: a sample ID, a patient ID identifying the patient from which the sample has been acquired, an operator ID identifying the operator initiating the analysis, information identifying the type of analysis performed, analysis results, a time at which the analysis has been performed, and/or the like.

Examples of other operational data forwarded to the medical device data management system may include one or more of the following: error conditions and/or other indications about a current operational state of the medical device, such as whether one or more types of measurements are currently available; information about required maintenance, calibration, refurbishment of consumables, etc. information about scheduled calibration tasks and/or other maintenance tasks, etc.

Generally, the information from the medical devices may be forwarded to the medical device data management system according to a suitable communications protocol.

Again referring to FIG. 1, the medical devices 103 may be located at respective locations throughout a hospital or other health care facility, e.g. on different wards, floors, stations, laboratories etc. Some of the medical devices may be of the same type. For example, some of the medical devices may be from the same manufacturer while others may be from different manufacturers. Moreover, devices—even if they are from the same manufacturer—may differ considerably, e.g. because they have different functions, communicate data in a different manner, etc. In the example of FIG. 1, four medical devices are shown, but it will be appreciated that, while a system with only four or less medical devices is possible, typical systems include more than four medical devices, such as considerably more medical devices, e.g. several tens or hundreds of medical devices.

The facility information system 102 may be embodied as a suitably programmed data processing system executing a facility information software application, such as a hospital information software application, or a corresponding suite of applications. The facility information system may be embodied as one or more server computers and one or more client computers or it may be implemented using another suitable computing infrastructure, e.g. one or more virtual servers, a cloud-based implementation, and/or the like. The facility information system may include a data warehouse and/or other suitable software components for managing at least some of the healthcare facility's, e.g. a hospital's, medical and administrative data.

The medical device data management system 101 is configured to communicate with the medical devices 103 to receive data from the medical devices, such as measurement/monitoring results, patient-related data, maintenance-related data, error messages, calibration data, status data, etc. The medical device data management system may further send information to some or all of the medical devices, such as patient-related data, commands, requests for information, etc. It will be appreciated that the nature and amount of data received from and/or sent to the medical devices may differ from device to device. The medical device data management system may further communicate data with the facility information system, such as patient-related data, device-related data (e.g. usage statistics, maintenance-related data, etc.) and/or the like. To this end, the medical device data management system may forward information directly between the medical devices and the facility information system and/or process at least some of the data and forward the processed data (e.g. accumulated usage statistics, etc.). In this respect, the medical device data management system may be regarded as operating as a gateway between the medical devices and the facility information system. The medical device data management system may further provide monitoring and/or quality assurance functions and/or other data management functions to users, e.g. by providing overviews over medical devices, their status, quality control data, etc.

The medical device data management system 101 is configured to communicate with the portable electronic devices 104 to send data to the portable electronic devices, such as availability predictions in respect of selected ones of the medical devices 103. The medical device data management system may further receive information from some or all of the portable electronic devices, such as operator-related data, location information, requests for information, etc. Embodiments of a process for providing availability predictions to the portable electronic devices will be described in greater detail below with reference to FIGS. 4-8.

The medical device data management system 101 may be embodied as a suitably programmed data processing system executing a medical device data management software and, optionally, further software, etc. The medical device data management system may be embodied as a single computer, as one or more server computers and one or more client computers, or using another suitable computing infrastructure, e.g. one or more virtual servers, a cloud-based implementation, and/or the like. It will be appreciated that the medical device data management system 101 and the facility information system 102 may share some or even all hardware components, e.g. they may be embodied as respective software applications that at least in part run on the same computers. It will further be appreciated that some or even all of the functions of the medical device data management system and the facility information system may be integrated into a single software and/or hardware system.

The medical device data management system comprises a medical device interface component 105 for communicating with the medical devices 103, a data management component 106 communicatively coupled to the device interface component, a portable device interface component 107 communicatively coupled to the data management component and for communicating with the portable electronic devices 104, a database 108 or a similar data storage device communicatively coupled to the data management component, and a HIS interface component 109 communicatively coupled to the data management component. It will be appreciated that the above components may be divided into separate hardware and/or software components or at least partly integrated into shared components. It will further be appreciated that the medical device data management system may comprise additional components such as a user interface component communicatively coupled to the data management component.

The medical device interface component 105 comprises suitable circuitry, firmware and/or software for communicating with the medical devices 103. In particular, the device interface component 105 may comprise a number of device drivers. Similarly, the portable device interface component 107 comprises suitable circuitry, firmware and/or software for communicating with the portable electronic devices 104, and the HIS interface component 109 comprises suitable circuitry, firmware and/or software for communicating with the facility information system 102. The medical device data management system 101 may communicate directly with the facility information system 102 or via one or more intermediary devices and/or software components. It will be appreciated that the various interface components 105, 107 and 109 may share some or even all hardware and/or software components, e.g. a common network adapter and/or common software implemented certain levels of a communication stack.

The database 108 may have stored thereon data related to the medical devices, such as log data, usage statistics, etc., operator-related data, etc. Alternatively or additionally, some of this data may be stored by the facility information system, i.e. some of the database 108 may reside on the facility information system.

The data management component 106 may comprise a central processing unit and associated hardware, such as memory, etc. The data management component 106 is suitably programmed to perform the data management functions of the medical device data management system described herein, including processing data communicated with the medical devices and the facility information system and processing data and communicating data with the portable electronic devices. The data processing performed by the data management component may include preparing information about selected connected medical devices for display by the portable electronic devices as described herein, including a predicted availability of selected medical devices.

Figure 4:
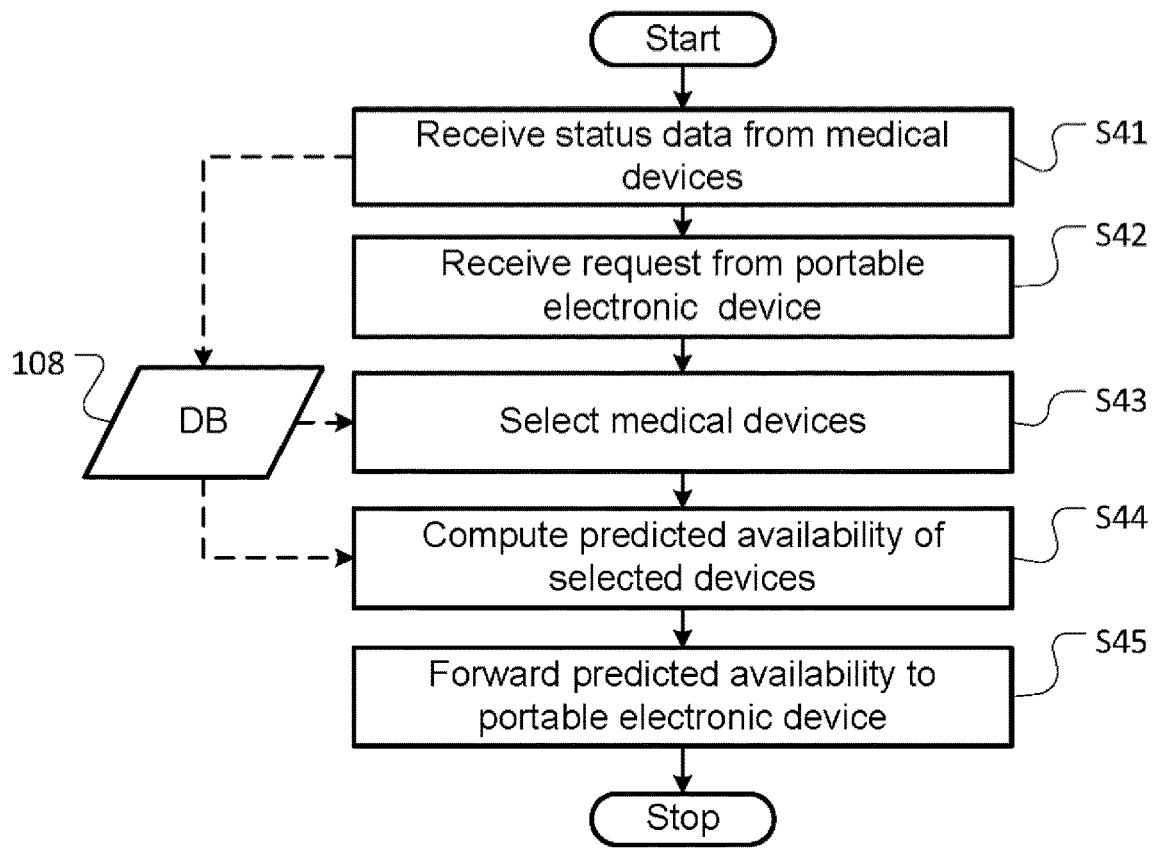
FIG. 4 schematically illustrates a process performed by an embodiment of a medical device data management system.

FIG. 4 schematically illustrates a process performed by an embodiment of a medical device data management system, e.g. a medical device data management system as described in connection with FIG. 1.

In step S41 the medical device data management system receives status information about the operational status of respective medical devices of the health care facility, e.g. from all medical devices that have been registered by the medical device management system. The operational status may include one or more of the following:
- a current operational status (e.g. "available", "out of service", "calibrating", "analyzing");
- scheduled times of calibration or other maintenance tasks;
- expected duration of ongoing calibration or other maintenance tasks;
- type of measurements currently available by the medical device;
- if the medical device includes multiple sample beds, information about how many sample beds are currently occupied by samples waiting to be analysed.

Some or all of the above information may be communicated by the medical devices to the medical device data management system in a number of ways. For example, each medical device may transmit regular status messages, e.g. a predetermined time intervals, in response to status requests by the medical device data management system or the like. Additionally or alternatively, the medical device may send status updates responsive to a change in status. The medical device data management system may maintain records in a database 108 indicative of the current and expected future status of the respective medical devices. Based on the received status information, the medical device data management system may thus update the status records.

In step S42, the medical device data management system receives a request for current status information from a portable electronic device. The request may include information identifying an operator of the portable electronic device. Alternatively, the portable electronic device may previously have been associated with a given operator, e.g. during a login process.

In step S43, the medical device data management system selects a subset of medical devices about which current status information is to be forwarded to the requesting portable electronic device. In the present embodiment, the selection is based on the identity of the operator and on information stored in a database 108 of the medical device data management system, or a database to which the medical device data management system has access to, e.g. a database of a HIS system. In particular, the database may have stored operator profile data associated with respective operators. The operator profile data associated with an operator may include a list of preferred medical devices. The list of preferred medical devices may include medical devices that have previously been specifically selected by the operator, e.g. by using functionality of the portable electronic device. Alternatively or additionally, the operator-specific list of preferred medical devices may be created or modified using historic usage statistics as will be described in greater detail below.

In step S44, the medical device data management system computes a predicted availability of the selected medical devices. This computation is based on the status records maintained in database 108. For example, for each medical device the predicted availability may include one or more of the following:
- an indicator of the currently available functionality of the medical device. This indicator may e.g. indicate whether the medical device is fully operational, operational with reduced accuracy, or non-operational. It will be appreciated that this indication may include alternative or additional indications, e.g. specific indications for respective types of measurements, etc.
- an indicator as to the current operational state. This indication may e.g. indicate whether the medical device is currently idle or performing a task, e.g. measuring, rinsing, calibrating, etc.
- an expected duration of the current operational state, e.g. an indication as to how long the currently performed task—optionally including any subsequent tasks that are placed in a queue—is expected to last or how long the medical device is expected to remain idle, e.g. based on information about scheduled calibration or other maintenance tasks.

It will be appreciated that, in other embodiments, alternative or additional indications may be provided.

Finally, in step S45, the medical device data management system forwards the computed predicted availability information associated with the selected medical devices to the portable electronic device for display by the portable electronic device. Accordingly, the operator of the portable electronic device is able to determine the current availability and the expected availability of the operator's preferred medical devices in real-time, e.g. when the operator obtains, or is about to obtain, a sample of biological material from a patient. In particular, the operator receives operator-specific information which allows the operator make fast decisions and the operator receives the information on the operator's portable electronic device, i.e. without having to first go to a stationary terminal, log in, and retrieve information. It will be appreciated that these indications may be presented in a number of ways on the display of the portable electronic device.

It will further be appreciated that, in other embodiments, various modifications to the process may be implemented. For example, the medical device data management system may compute and forward predicted availabilities of all, or at least a large subset of, medical devices to the portable electronic device. The selection of medical devices about which predicted availabilities are to be displayed may then be performed by the portable electronic device, e.g. based on a locally stored, operator-specific list of preferred medical devices. Similarly, in some embodiments, the medical device data management system may forward computed predicted availabilities at regular intervals and/or when predictions have changed without waiting for a request from a portable electronic device.

Figure 5:
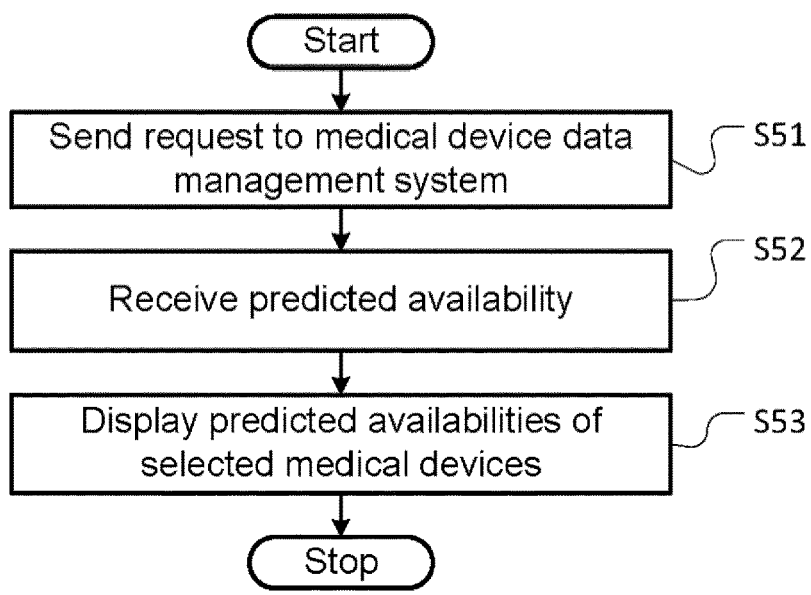
FIG. 5 schematically illustrates the corresponding steps performed by an embodiment of a portable electronic device.

FIG. 5 schematically illustrates the corresponding steps performed by an embodiment of a portable electronic device, e.g. a portable electronic device as described in connection with FIGS. 1 and 2, communicatively coupled to the medical device data management system that performs the process of FIG. 4.

In step S51, the portable electronic device sends a request for current status information to the medical device data management system. For example, the portable electronic device may send such requests at regular intervals or triggered by an event, e.g. by a user input. The request may include information identifying an operator of the portable electronic device.

In step S52, the portable electronic device receives computed predicted availability information associated with selected medical devices from the medical device data management system.

In step S53, the portable electronic device displays the received information about the predicted availability, optionally only for a selected subset of the medical devices for which predicted availabilities have been received.

Figure 6:
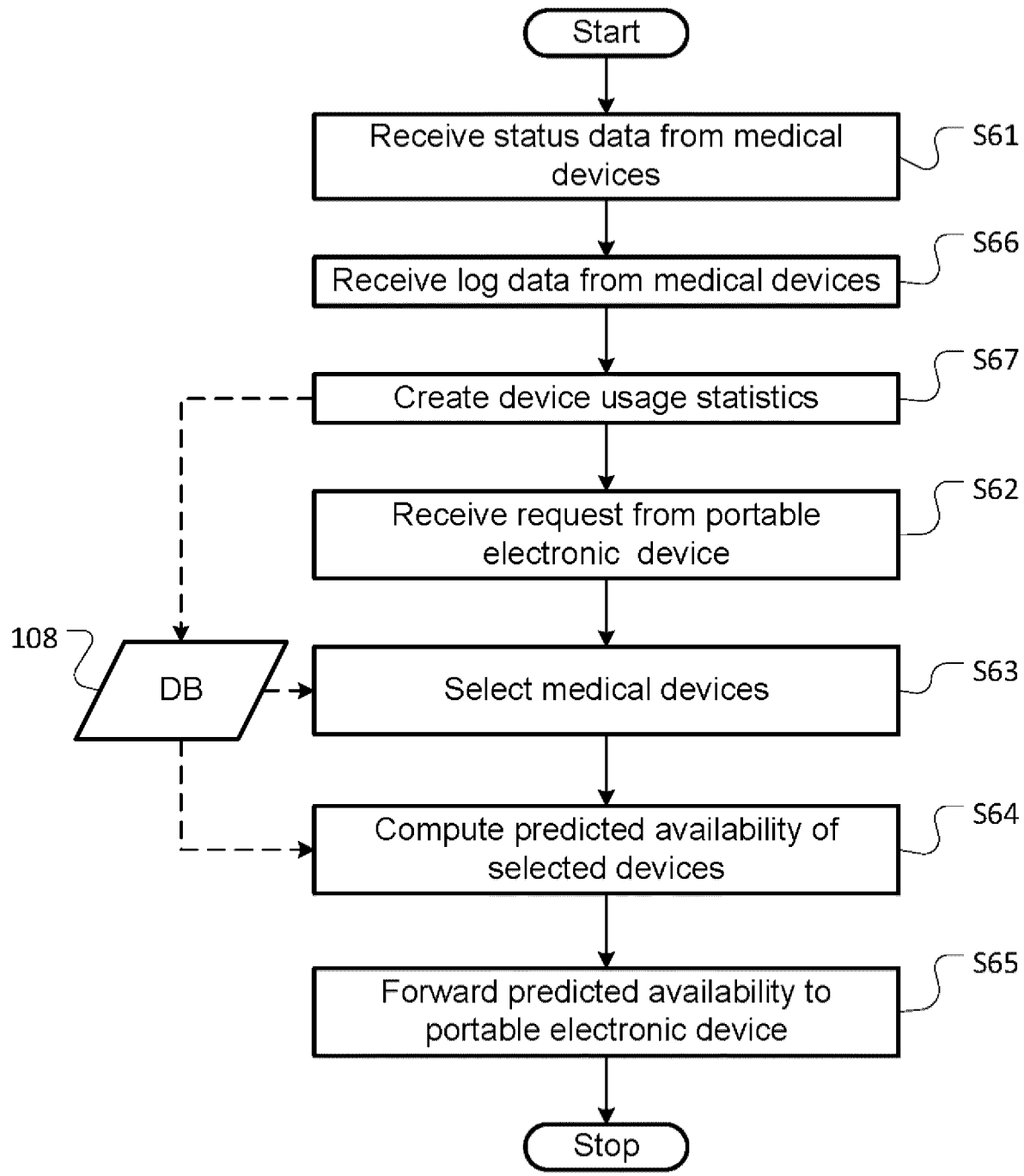
FIG. 6 schematically illustrates a process performed by an embodiment of a medical device data management system.

FIG. 6 schematically illustrates another example of a process performed by an embodiment of a medical device data management system, e.g. a medical device data management system as described in connection with FIG. 1. The process is similar to the process of FIG. 4 except that, in the process of FIG. 6, the medical device data management system utilizes log data from the medical devices to select the medical devices for which information about predicted availabilities is forwarded to a portable electronic device.

In particular, in step S61 the medical device data management system receives status information about the operational status of respective medical devices of the health care facility, as described in connection with step S41 of the process of FIG. 4.

In step S66, the medical device data management system receives log data pertaining to measurements performed by the medical devices on respective samples of biological material. For example, for each measurement some or all of the following information may be forwarded by the medical device:
- time of measurement
- a type of measurement, e.g. which physiological parameters have be measured, such as which analytes the sample has been analysed for;
- Information identifying the medical device;
- Information identifying the operator having initiated the analysis;
- Information identifying the sample that was analysed;
- Information identifying the patient from which the sample was taken;
- Information about the result of the analysis, optionally including any error messages.

A medical device may forward the log data pertaining to a measurement when the measurement has been taken; alternatively, the medical device may store results from multiple measurements in a local buffer of the medical device and forward the log data at a later point in time, e.g. upon a request from the medical device data management system. The medical device data management system may store the received log data in database 108.

In step S67, the medical device data management system computes usage statistics from the received log data and stores the computed usage statistics in database 108. The computation of usage statistics may be performed regularly, e.g. daily, weekly, etc. Alternatively, the process may compute the statistics on the fly if and when the need arises.

In particular, the medical device data management system may determine the most frequently used medical devices for each operator, e.g. the most frequently used devices during a predetermined time window, e.g. the previous week or month. Alternatively or additionally, the medical device data management system may determine the most recently used medical devices by each operator. This information may then be used by the medical device data management system to select, for a given operator, the medical devices for which information about predicted availabilities is to be forwarded to a portable electronic device associated with the operator.

Alternatively or additionally, the medical device data management system may compute an average workload of the respective medical devices, e.g. as a function of the time of day and/or as a function of the days of the week. This information may then be used by the medical device data management system when computing the predicted availability of selected medical devices.

In step S62, the medical device data management system receives a request for current status information from a portable electronic device, as described in connection with step S42 of the process of FIG. 4.

In step S63, the medical device data management system selects a subset of medical devices about which current status information is to be forwarded to the requesting portable electronic device. In the present embodiment, the selection is based on the identity of the operator and on information stored in a database 108 of the medical device data management system. In particular, the medical device data management system may select medical devices based on the computed usage statistics, e.g. by selecting the most frequently used medical devices by the operator in question. It will be appreciated that the selection may combine multiple criteria, e.g. by selecting, for a given operator, the most frequently used medical devices, a number of manually selected medical devices and/or the most recently used medical devices by said operator.

In addition or alternatively to a selection based on usage statistics, the medical device management system may also use other criteria, e.g. location-based criteria, for selecting medical devices. For example, the medical device data management system may maintain location information about the respective medical devices. This information may e.g. be maintained in database 108. The medical device data management system may further obtain dynamic location information about a current location of the portable electronic device that requests information. For example, the dynamic location information about the portable electronic device may be obtained using a Wi-Fi location determination or another suitable mechanism for determining a location of the portable electronic device within the health care facility. The medical device data management system may then select the medical devices that are closest to the current location of the portable electronic device.

In step S64, the medical device data management system computes a predicted availability of the selected medical devices. This computation is based on the status records maintained in database 108. For example, in addition or alternatively to the indications described in connection with step S44 of FIG. 4, the medical device data management system may compute an estimated delay or waiting period to be expected when using the respective selected medical devices where the calculation is based on the current operational status, the expected duration of said status and the typical current workload of the medical device, e.g. at the current time of day, day of the week, and/or the like.

Finally, in step S65, the medical device data management system forwards the computed predicted availability information associated with the selected medical devices to the portable electronic device for display by the portable electronic device, as described in connection with step S45 of FIG. 4.

It will be appreciated that a number of modifications of the process of FIG. 6 are possible, e.g. as described in connection with FIG. 4. Moreover, it will be appreciated that the process of FIG. 6 may cooperate with a process performed by a portable electronic device as described in connection with FIG. 5.

Figure 7:
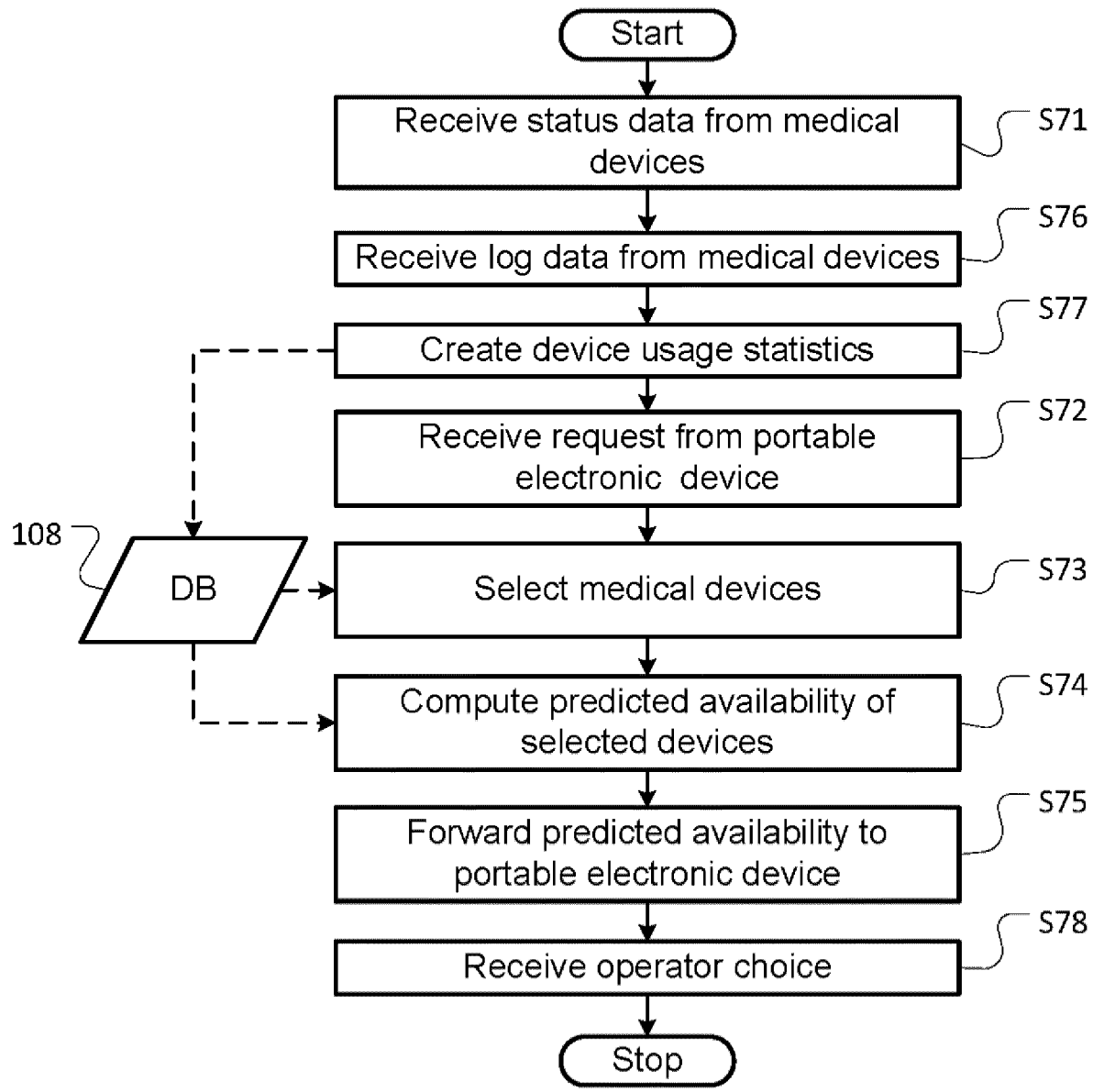
FIG. 7 schematically illustrates a process performed by an embodiment of a medical device data management system.

FIG. 7 schematically illustrates yet another example of a process performed by an embodiment of a medical device data management system, e.g. a medical device data management system as described in connection with FIG. 1. The process is similar to the process of FIG. 6 except that, in the process of FIG. 7, the medical device data management system further receives and utilizes information from the portable electronic devices about intended future measurements.

In particular, steps S71, S76, S77, S72 and S73 correspond to steps S61, S66, S67, S62 and S63, respectively, of the process of FIG. 6. Hence, these steps will not be described in detail again.

In step S74, the medical device data management system computes a predicted availability of the selected medical devices. This computation is based on the status records maintained in database 108 as described in connection with step S64 of the process of FIG. 6. However, in the present embodiment, the process further utilizes indications received from the portable electronic devices of respective operators about intended measurements to be taken by said operators. For example, when selecting a medical device based on the displayed predicted availabilities of selected medical devices on their portable electronic devices, the operator may indicate this selection, e.g. by tapping the corresponding entry on a list of medical devices on the display of the portable electronic device. These indications are then communicated from the portable electronic devices to the medical device management system where they are recorded.

The medical device data management system may then compute an estimated delay or waiting period for the respective selected medical devices where the calculation is based on the current operational status, the expected duration of said status and the typical current workload of the medical device, e.g. at the current time of day, day of the week, and/or the like and based on the received indications. For example, if fewer than normal indications are received at a given time, the estimated waiting period computed by the medical device data management system may be scaled downwards accordingly.

In step S75, the medical device data management system forwards the computed predicted availability information associated with the selected medical devices to the portable electronic device for display by the portable electronic device, as described in connection with step S65 of FIG. 6.

Finally, in step S78, the medical device data management system receives and records an indication from the portable electronic device about which medical device the operator has chosen.

It will be appreciated that a number of modifications of the process of FIG. 7 are possible, e.g. as described in connection with FIGS. 4 and/or 6.

Figure 8:
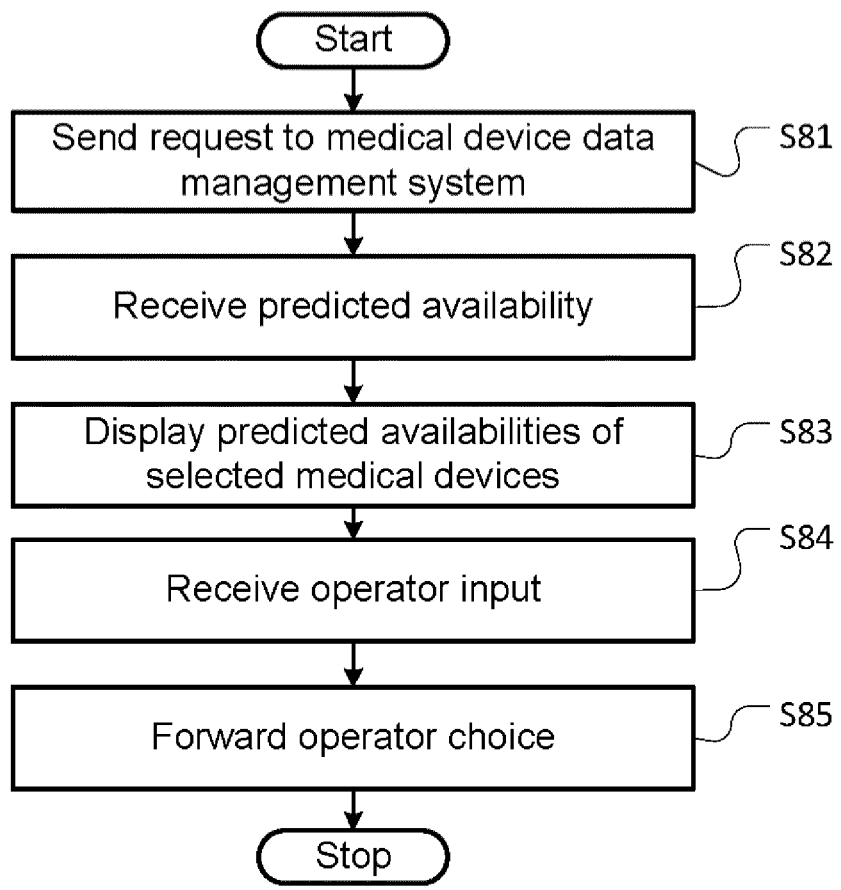
FIG. 8 schematically illustrates the corresponding steps performed by an embodiment of a portable electronic device.

FIG. 8 schematically illustrates the corresponding steps performed by an embodiment of a portable electronic device, e.g. a portable electronic device as described in connection with FIGS. 1 and 2, communicatively coupled to the medical device data management system that performs the process of FIG. 7.

In step S81, the portable electronic device sends a request for current status information to the medical device data management system. For example, the portable electronic device may send such requests at regular intervals or triggered by an event, e.g. a user input. The request may include information identifying an operator of the portable electronic device.

In step S82, the portable electronic device receives computed predicted availability information associated with selected medical devices from the medical device data management system.

In step S83, the portable electronic device displays the received predicted availability, optionally only for a selected subset of the medical devices for which predicted availabilities have been received.

In step S84, the portable electronic device receives a user input indicative of a choice made by the operator of which medical device the operator intends to use for a current sample of biological material.

In step S85, the portable electronic device forwards information about which medical device the operator has chosen to the medical device management system.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. In view of the foregoing, it is intended that the present invention cover modifications and variations of this invention provided they fall within the scope of the following claims and their equivalents.

In apparatus claims enumerating several features, several of these features can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in the present disclosure is taken to specify the presence of stated features, integers, steps or components but does not preclude the presence or addition of one or more other features, integers, steps, components or groups thereof.

The invention claimed is:

1. A system of medical devices, the system comprising:
a medical device data management system comprising a processor;
a plurality of medical devices communicatively connected to the medical device data management system; each of the medical devices being operable to analyze one or more samples of biological material; and to communicate information about an operational state of the medical device to the medical device data management system; and
a plurality of portable electronic devices, each of the portable electronic devices operable to be carried by an operator, each of the portable electronic devices communicatively connectable to the medical device data management system and configured to receive, from the medical device data management system, information indicative of an operational state of each of the medical devices and to display the received information in respect of one or more selected devices of the medical devices,
wherein:

the information about an operational state received by the portable electronic device from the medical device data management system includes an availability prediction;

one or more of the portable electronic devices are configured to transmit, to the medical device data management system, an indication of an intended measurement to be taken on a biological sample by an operator associated with the portable electronic device; and wherein the medical device data management system is configured to determine the availability prediction based at least in part on the information received from the medical devices and on the indications received from the one or more portable electronic devices; and the medical device data management system is configured to:

obtain device location information about respective locations of at least a subset of the medical devices and operator location information about a location of said operator; and determine the availability prediction at least in part on the information received from the medical devices, on the indications received from the one or more portable electronic devices and on the obtained device location information and operator location information.

2. The system according to claim 1; wherein each medical device is configured to communicate an availability prediction to the medical device data management system.

3. The system according to claim 1; wherein the medical device data management system is configured to:

obtain usage data associated with at least a subset of medical devices, the usage data being indicative of a frequency of use of each of said subset of medical devices; and determine the availability prediction based at least in part on the obtained usage data.

4. The system according to claim 1; wherein the medical device data management system is configured to:

obtain device location information for at least a subset of the medical devices;

select one or more of the medical devices based at least in part on the obtained device location information and on an identity of an operator associated with the one of the portable electronic devices; and transmit, to said portable electronic device associated with said operator, information indicative of an operational state of the selected one or more medical devices for display by said portable electronic device.

5. The system according to claim 4; wherein the medical device data management system is configured to:

obtain dynamic operator location information about a current location of said operator;

select the one or more of the medical devices to be associated with said operator based at least in part on the obtained device location information and the obtained operator location information.

6. The system according to claim 1; wherein the medical device data management system is configured to obtain a location of a portable electronic device associated with the operator and to determine the operator location information to coincide with the obtained location of the portable electronic device.

7. The system according to claim 1; wherein the medical device data management system is configured to:

obtain usage data associated with an operator, the usage data being indicative, for at least a subset of the medical devices, of a frequency of use of each of said subset of the medical devices by said operator;

select one or more of the medical devices to be associated with said operator based at least in part on the obtained usage data; and transmit, to a portable electronic device associated with said operator, information indicative of an operational state of the selected one or more medical devices for display by said portable electronic device.

8. The system according to claim 1, wherein:

a first one of the medical devices comprises multiple sample bays, wherein each sample bay is configured to receive a sample of biological material to be analyzed by the first medical device;

the first medical device is configured to analyze samples positioned in the sample bays in a sequential order to implement a queue of said samples placed in the sample bays and awaiting analysis by the first medical device;

the first medical device is configured to communicate information indicative of a current status of said queue to the medical device data management system; and the medical device data management system is configured to determine the operational state of the first medical device from at least the communicated information indicative of said current status of said queue.

9. The system according to claim 1, wherein the availability prediction is selected from the group consisting of information indicative of a predicted availability of a medical device for performing an analysis, information indicative of an estimated duration until a medical device is available for operation, information indicative of an estimated duration until the medical device is unavailable for operation, information indicative of an estimated duration a sample is expected to wait in a queue until being analyzed, information about scheduled maintenance events and/or the estimated duration thereof, and combinations thereof.

10. A system comprising:

a plurality of medical devices, a plurality of portable electronic devices, and a medical device data management system comprising a processor, wherein the medical device data management system is communicatively connectable to the plurality of medical devices, each medical device is operable to analyze one or more samples of biological material;

the medical device data management system is communicatively connectable to the plurality of portable electronic devices, and each portable electronic device is configured to receive, from the medical device data management system, information indicative of an operational state of one or more selected ones of the medical devices and to display the received information, wherein:

the information about an operational state received by the portable electronic device from the medical device data management system includes an availability prediction;

the medical device data management system is configured to:

receive information about operational states of respective ones of the medical devices; and communicate information indicative of an operational state of one or more selected ones of the medical devices to a selected one of the portable electronic devices;

one or more of the portable electronic devices are configured to transmit, to the medical device data management system, an indication of an intended measurement to be taken on a biological sample by an operator associated with the portable electronic device; and wherein the medical device data management system is configured to determine the availability prediction based at least in part on the information received from the medical devices and on the indications received from the one or more portable electronic devices; and the medical device data management system is configured to:

obtain device location information about respective locations of at least a subset of the medical devices and operator location information about a location of said operator; and determine the availability prediction at least in part on the information received from the medical devices, on the indications received from the one or more portable electronic devices and on the obtained device location information and operator location information.

11. The system according to claim 10, wherein the availability prediction is selected from the group consisting of information indicative of a predicted availability of a medical device for performing an analysis, information indicative of an estimated duration until a medical device is available for operation, information indicative of an estimated duration until the medical device is unavailable for operation, information indicative of an estimated duration a sample is expected to wait in a queue until being analyzed, information about scheduled maintenance events and/or the estimated duration thereof, and combinations thereof.

12. A non-transitory computer readable medium comprising executable program code configured, when executed by a medical device data management system communicatively connectable to a plurality of medical devices, each medical device being operable to analyze one or more samples of biological material, and to a plurality of portable electronic devices, each configured to receive, from the medical device data management system, information indicative of an operational state of one or more selected ones of the medical devices and to display the received information, to cause the medical device data management system to:

receive information about operational states of respective ones of the medical devices; and communicate information indicative of an operational state of one or more selected ones of the medical devices to a selected one of the portable electronic devices, wherein:

the information about an operational state includes an availability prediction;

one or more of the portable electronic devices are configured to transmit, to the medical device data management system, an indication of an intended measurement to be taken on a biological sample by an operator associated with the portable electronic device; and wherein the medical device data management system is configured to determine the availability prediction based at least in part on the information received from the medical devices and on the indications received from the one or more portable electronic devices; and the medical device data management system is configured to:

obtain device location information about respective locations of at least a subset of the medical devices and operator location information about a location of said operator; and determine the availability prediction at least in part on the information received from the medical devices, on the indications received from the one or more portable electronic devices and on the obtained device location information and operator location information.

13. The non-transitory computer readable medium according to claim 12, wherein the availability prediction is selected from the group consisting of information indicative of a predicted availability of a medical device for performing an analysis, information indicative of an estimated duration until a medical device is available for operation, information indicative of an estimated duration until the medical device is unavailable for operation, information indicative of an estimated duration a sample is expected to wait in a queue until being analyzed, information about scheduled maintenance events and/or the estimated duration thereof, and combinations thereof.

14. A portable electronic device comprising a communications interface for data communication between the portable electronic device and a medical device data management system; a processor and a display; wherein the processor is configured to:

receive, from the medical device data management system via the communications interface, information indicative of an operational state of one or more selected ones of a plurality of medical devices connected to the data management system, each medical device being operable to analyze one or more samples of biological material; and to display on said display the received information, wherein:

the information indicative of an operational state includes an availability prediction;

the portable electronic device is configured to transmit, to the medical device data management system, an indication of an intended measurement to be taken on a biological sample by an operator associated with the portable electronic device; and wherein the medical device data management system is configured to determine the availability prediction based at least in part on the information received from the medical devices and on the indications received from the portable electronic device; and the medical device data management system is configured to:

obtain device location information about respective locations of at least a subset of the medical devices and operator location information about a location of said operator; and determine the availability prediction at least in part on the information received from the medical devices, on the indications received from the portable electronic device and on the obtained device location information and operator location information.

15. The portable electronic device according to claim 14, wherein the availability prediction is selected from the group consisting of information indicative of a predicted availability of a medical device for performing an analysis, information indicative of an estimated duration until a medical device is available for operation, information indicative of an estimated duration until the medical device is unavailable for operation, information indicative of an estimated duration a sample is expected to wait in a queue until being analyzed, information about scheduled maintenance events and/or the estimated duration thereof, and combinations thereof.

16. A non-transitory computer readable medium comprising executable program code configured, when executed by a processor of a portable electronic device, the portable electronic device comprising a communications interface for data communication between the portable electronic device and a medical device data management system, the processor and a display, to cause the processor to:
receive, from the medical device data management system via the communications interface, information indicative of an operational state of one or more selected ones of a plurality of medical devices connected to the data management system, each medical device being operable to analyze one or more samples of biological material; and to
display on said display the received information,
wherein:
the information indicative of an operational state includes an availability prediction;
the portable electronic device is configured to transmit, to the medical device data management system, an indication of an intended measurement to be taken on a biological sample by an operator associated with the portable electronic device; and wherein the medical device data management system is configured to determine the availability prediction based at least in part on the information received from the medical devices and on the indications received from the portable electronic device; and
the medical device data management system is configured to:
obtain device location information about respective locations of at least a subset of the medical devices and operator location information about a location of said operator; and
determine the availability prediction at least in part on the information received from the medical devices, on the indications received from the portable electronic device and on the obtained device location information and operator location information.

17. The non-transitory computer readable medium according to claim 16, wherein the availability prediction is selected from the group consisting of information indicative of a predicted availability of a medical device for performing an analysis, information indicative of an estimated duration until a medical device is available for operation, information indicative of an estimated duration until the medical device is unavailable for operation, information indicative of an estimated duration a sample is expected to wait in a queue until being analyzed, information about scheduled maintenance events and/or the estimated duration thereof, and combinations thereof.

* * * * *

UNITED STATES PATENT AND TRADEMARK OFFICE
CERTIFICATE OF CORRECTION

Page 1 of 1

PATENT NO. : 11,728,027 B2
APPLICATION NO. : 16/771785
DATED : August 15, 2023
INVENTOR(S) : Thomas Junker, Jakob Skov and Halina Tomaszewska It is certified that error appears in the above-identified patent and that said Letters Patent is hereby corrected as shown below:

On the Title Page

Item (72), Line 2, "Jakob Skov, Brønshøj (DE);" should read --Jakob Skov, Brønshøj (DK);--.

Signed and Sealed this
Fifth Day of March, 2024

Katherine Kelly Vidal
*Director of the United States Patent and Trademark Office*